United States Patent
Oikawa et al.

(10) Patent No.: US 6,828,459 B2
(45) Date of Patent: Dec. 7, 2004

(54) METHOD FOR PRODUCING CYCLOHEXANONE OXIME

(75) Inventors: Miyuki Oikawa, Niihama (JP); Masami Fukao, Ritto (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/457,383

(22) Filed: Jun. 10, 2003

(65) Prior Publication Data

US 2004/0002619 A1 Jan. 1, 2004

(30) Foreign Application Priority Data

Jun. 28, 2002 (JP) ........................................ 2002-189450

(51) Int. Cl.[7] ..................... C07C 249/04; C07C 249/06; C07C 249/12
(52) U.S. Cl. ...................................................... 564/253
(58) Field of Search ................................ 564/253, 259

(56) References Cited

U.S. PATENT DOCUMENTS

| | | | |
|---|---|---|---|
| 4,745,221 A | 5/1988 | Roffia et al. | |
| 5,227,525 A | 7/1993 | Tonti et al. | |
| 5,312,987 A | 5/1994 | Mantegazza et al. | |
| 5,498,793 A | * 3/1996 | Mantegazza et al. | ....... 564/265 |
| 5,683,952 A | 11/1997 | Onozawa et al. | |
| 5,691,266 A | 11/1997 | Onozawa et al. | |
| 5,736,479 A | 4/1998 | Schodel et al. | |
| 5,874,596 A | 2/1999 | Onozawa et al. | |
| 6,566,555 B2 | * 5/2003 | Thiele et al. | ............... 564/262 |
| 2002/0058840 A1 | 5/2002 | Thiele et al. | |

FOREIGN PATENT DOCUMENTS

EP 1 191 017 A2 * 3/2002 ......... C07C/249/04

* cited by examiner

Primary Examiner—Brian Davis
(74) Attorney, Agent, or Firm—Birch, Stewart, Kolasch & Birch, LLP

(57) ABSTRACT

A cyclohexanone oxime is produced in a method comprising the step of reacting a cyclohexanone with a hydrogen peroxide and an ammonia in the presence of a titanium silicate and a silicon compound other than the titanium silicate. In the method, the reaction is conducted with suppressing the inactivation of the titanium silicate as a catalyst, to produce the cyclohexanone oxime with a high yield.

5 Claims, No Drawings

METHOD FOR PRODUCING CYCLOHEXANONE OXIME

BACKGROUND OF THE INVENTION

1. Field of the Invention

The present invention relates to a method for producing a cyclohexanone oxime from a cyclohexanone using ammonia and hydrogen peroxide. The cyclohexanone oxime is useful as a starting material for producing an ε-caprolactam, or the like.

2. Description of the Related Art

For producing a cyclohexanone oxime, there has been proposed a method of reacting cyclohexanone with hydrogen peroxide and ammonia in the presence of titanium silicate catalyst (e.g., Japanese Patent Application Laid-Open No. (JP-A-)62-59256 corresponding to U.S. Pat. No. 4,745,221; JP-A-6-49015 corresponding to U.S. Pat. No. 5,312,987; JP-A-6-92922 corresponding to U.S. Pat. No. 5,227,525; and JP-A-7-100387 corresponding to U.S. Pat. Nos. 5,683,952, 5,691,266 and 5,874,596). Such a method has advantages in that it does not need to neutralize sulfuric acid with ammonia, while the neutralization is conducted in the conventional method for producing cyclohexanone oxime with hydroxylamine sulfate, and in that product separation from the catalyst can be readily carried out since a solid catalyst is utilized.

However, in the above-reaction of cyclohexanone with hydrogen peroxide and ammonia, a catalytic activity of the titanium silicate catalyst is gradually deteriorated with a passage of reaction time so that the conversion rate of cyclohexanone may be insufficient.

SUMMARY OF THE INVENTION

One of objects of the present invention is to provide a method in which inactivation of the titanium silicate is suppressed in a reaction of cyclohexanone with hydrogen peroxide and ammonia, thereby producing a cyclohexanone oxime in high yield.

As a result of eager study by the present inventors, it has been found that the above object and other objects can be achieved by performing the reaction of cyclohexanone in the presence of a titanium silicate together with a silicon compound other than the titanium silicate, and the present invention has been accomplished.

The present invention provides a method for producing a cyclohexanone oxime, the method comprising the step of reacting a cyclohexanone with hydrogen peroxide and ammonia in the presence of a titanium silicate and a silicon compound other than the titanium silicate.

DESCRIPTION OF THE INVENTION

In the present invention, a cyclohexanone oxime is produced by an ammoximation of cyclohexanone, in which a cyclohexanone is reacted with hydrogen peroxide and ammonia in the presence of a titanium silicate and a silicon compound other than the titanium silicate.

A titanium silicate to be used in the present invention may be a zeolite comprising titanium, silicon and oxygen as elements in its skeletal structure. The titanium silicate may have a skeletal structure substantially constituted of titanium, silicon and oxygen, or of an optional other elements in addition to these elements. The titanium silicate may have an atomic ratio of silicon to titanium of from 10 to 1000, and may have the shape of fine powder, pellet or the like. The titanium silicate can be prepared by a method disclosed in JP-A-56-96720 corresponding to U.S. Pat. No. 4,410,501 or the like.

In the present invention, by using such a titanium silicate and a silicon compound other than the titanium silicate, a cyclohexanone is reacted with hydrogen peroxide and ammonia to obtain a cyclohexanone oxime.

A cyclohexanone to be used as a starting material in the prevent invention may be obtained, for example, by oxidation of a cyclohexane, by hydration of a cyclohexene, followed by dehydrogenation, or by hydrogenation of a phenol.

The hydrogen peroxide to be used in the prevent invention may be produced by the so-called anthraquinone method. The anthraquinone method can be conducted, for example, by a process in which an α-ethylanthraquinone is dissolved in a water-insoluble solvent such as a benzene, which is then subjected to catalytic hydrogenation reaction to obtain a hydroanthraquinone, and the hydroanthraquinone is oxidized to an α-ethylanthraquinone while providing hydrogen peroxide. Commercially available hydrogen peroxide, which is an aqueous solution having a concentration of about 10% by weight to about 70% by weight, may also be used in the present invention. The relative molar amount of the hydrogen peroxide is preferably in the range of from about 0.5 mol to about 3 mol, and is more preferably in the range of from about 0.5 mol to about 1.5 mol, based on 1 mol the cyclohexanone. The hydrogen peroxide used in the present invention may contain a stabilizer including, for example, a phosphate salt such as a sodium phosphate, a polyphosphate salt such as a sodium pyrophosphate and a sodium tripolyphosphate, a pyrophosphoric acid, an ascorbic acid, an ethylenediamine-tetraacetic acid, a nitro tri-acetic acid, an amino tri-acetic acid, a diethylenetriamino penta-acetic acid, and the like.

In the present invention, ammonia may be used in a gaseous form, in a liquid form, or in a solution form using water, an organic solvent or the like. The relative molar amount of the ammonia is preferably about 1 mol or more, and is more preferably about 1.5 mol or more, based on 1 mol of the cyclohexanone.

The reaction for producing a cyclohexanone oxime with ammonia and hydrogen peroxide may be performed in a solution using a solvent. Examples of the solvent include an alcohol such as a methyl alcohol, an ethyl alcohol, a n-propyl alcohol, an isopropyl alcohol, a n-butyl alcohol, a sec.-butyl alcohol, a tert.-butyl alcohol and a tert.-amyl alcohol; water; and a mixture thereof.

In the present invention, the reaction for producing a cyclohexanone oxime using ammonia and hydrogen peroxide is performed in the presence of a titanium silicate together with a silicon compound other than the titanium silicate. (Hereinafter, the silicon compound other than the titanium silicate may be simply referred to as "silicon compound" in some cases). By using the silicon compound with the titanium silicate, inactivation of the titanium silicate can be suppressed, and therefore, the amount of the titanium silicate to be used as the catalyst in the reaction can be reduced. In view of cost reduction, it is preferred to use a less expensive silicon compound than a titanium silicate, which is usually relatively expensive. The silicon compound, in itself, may substantially have no catalytic activity in the reaction.

Examples of the silicon compound include a compound containing silicon and oxygen, such as a silica gel, a silicic acid and a silicate. Also, a crystalline silica gel and a metallo-silicate, each of which has a zeolite-like structure, are preferably used. The silicon compound may be used singly, or two or more of the silicon compounds may be used in combination, if necessary.

In the present invention, the titanium silicate and silicon compound are preferably used in a concentration, respectively, of from about 0.1% by weight to about 10% by weight based on the liquid portion of the reaction mixture, so that the titanium silicate and silicon compound are suspended in the mixture.

The effect of suppressing the inactivation of catalytic activity of the titanium silicate is remarkable especially when water is present in the reaction mixture at a concentration of about 10% by weight or more.

The reaction for producing a cyclohexanone oxime using ammonia and hydrogen peroxide may be conducted batch-wise, or may be conducted in a continuous manner. The batch-wise reaction may be carried out, for example, by a method in which a reactor is charged with a cyclohexanone, ammonia, a titanium silicate, a silicon compound and a solvent, into which hydrogen peroxide is introduced, while stirring; or by a method in which a reactor is charged with a cyclohexanone, a titanium silicate, a silicon compound and a solvent, into which hydrogen peroxide and ammonia are introduced, whole stirring; or by a method in which a reactor is charged with a titanium silicate, a silicon compound and a solvent, into which a cyclohexanone, hydrogen peroxide and ammonia are introduced, while stirring. The continuous reaction may be carried out, for example, by a method in which a suspension of a titanium silicate and a silicon compound is prepared in a reactor, into while a cyclohexanone, hydrogen peroxide, ammonia and a solvent are further introduced, while a liquid portion of the resulting reaction mixture is extracted through a filter from the reactor. It is preferred to use a glass-lining reactor, a stainless steel reactor or the like in view of avoiding decomposition of the hydrogen peroxide.

The reaction temperature may be in the range of from about 50° C. to 100° C. The reaction may be performed at a normal pressure, and is preferably under pressure in order to increase the solubility of ammonia into a liquid portion of the reaction mixture. In the case of the reaction under pressure, the pressure may be adjusted by using an inert gas such as nitrogen gas and helium gas.

The post handling procedures, such as separation of the cyclohexanone oxime from the reaction mixture, is not limited and may be carried out appropriately using a known methods. For example, the separation of the cyclohexanone oxime may be conducted in a manner such that the titanium silicate and silicon compound is separated from the reaction mixture by filtration or the like to obtain a liquid portion of the reaction mixture, followed by distillation of the liquid portion.

In accordance with the present invention, a cyclohexanone is reacted with hydrogen peroxide and ammonia with suppressing the inactivation of a titanium silicate as a catalyst, to produce a cyclohexanone oxime in high yield.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2002-189450 filed on Jun. 28, 2002, indicating specification, claims and summary, are incorporated herein by reference in their entirety.

EXAMPLE

The present invention is described in more detail by reference to the following Examples, which should not be construed as a limitation upon the scope of the present invention.

In Examples and Comparative Examples, the cyclohexanone and the cyclohexanone oxime were analyzed by gas-chromatography, and the conversion of cyclohexanone, the selectivity to cyclohexanone oxime and the yield of cyclohexanone oxime were calculated on the basis of the analytical results.

Example 1

A one (1) L autoclave as a reactor was charged with a cyclohexanone, a water-containing t-butyl alcohol (containing 12% by weight of water) and a 60% by weight of hydrogen peroxide at a rate of 67 g/hour, 252 g/hour and 43 g/hour, respectively. At the same time, ammonia was supplied into the reactor so as to be present at the concentration of 2% by weight based on the liquid portion of the resulting reaction mixture, while the liquid portion of the reaction mixture was discharged from the reactor through a filter, to conduct the reaction, continuously. During the reaction, a titanium silicate and a silica gel (trade name: WAKO GEL LP-20, obtained from Wako Pure Chemical Industries, Ltd.) were placed in the reactor in amounts of 0.9% by weight and 6% by weight, respectively, based on the liquid portion of the reaction mixture. The continuous reaction was performed at a temperature of 85° C. in a pressure of 0.25 MPa with a retention time of 72 minutes. As a result of analysis of the liquid portion obtained after 5.5 hours of the reaction, the conversion of the cyclohexanone was 99.1%, the selectivity to cyclohexanone oxime was 99.5%, and the yield of cyclohexanone oxime was 98.6%.

Comparative Example 1

The continuous reaction was conducted in the same manner as in Example 1, except that the amount of the titanium silicate was changed from 0.9% by weight to 1.3% by weight based on the liquid portion of the reaction mixture, and the silica gel was not used. As a result, the conversion of the cyclohexanone was 98.6%, the selectivity to cyclohexanone oxime was 99.5%, and the yield of cyclohexanone oxime was 98.1%.

It was found that, although the amount of titanium silicate used in Comparative Example 1 was more than that in Example 1 (the amounts being 1.3% by weight and 0.9% by weight, respectively, based on the liquid portions of the reaction mixtures), the conversion of cyclohexanone in Comparative Example 1 was almost equal to or less than that in Example 1 since the silica gel was not used in Comparative Example 1.

Comparative Example 2

The continuous reaction was conducted in the same manner as in Example 1, except that the amount of the titanium silicate was changed from 0.9% by weight to 1.2% by weight based on the liquid portion of the reaction mixture, and the silica gel was not used. As a result, the conversion of the cyclohexanone was 93.0%, the selectivity to cyclohexanone oxime was 99.0%, and the yield of cyclohexanone oxime was 92.1%.

It was found that, although the amount of titanium silicate used in Comparative Example 2 was more than that in Example 1 (the amounts being 1.2% by weight and 0.9% by weight, respectively, based on the liquid portions of the reaction mixtures), the conversion of cyclohexanone in Comparative Example 2 was about 6% by weight less than that in Example 1 since the silica gel was not used in Comparative Example 2.

Example 2

A 200 mL autoclave (made from SUS316) as a reactor was charged with a cyclohexanone (12.8 g), a 25% by weight of ammonia water (13.2 g), a water-containing t-butyl alcohol (19.7 g) (containing 13% by weight of water), a titanium silicate (1 g) and a silicic acid (3 g) (obtained from Nakalai Chemicals Co., Ltd at a temperature of 80° C. while stirring. In to the reactor, 30% hydrogen peroxide (14.9 g) was supplied over 55 minutes, and the resulting reaction mixture was maintained for 35 minutes. The catalysts were separated from the reaction mixture and the remaining liquid portion was analyzed. As a result, the conversion of the cyclohexanone was 70.9%, the selectivity to cyclohexanone oxime was 74.4% and the yield of cyclohexanone oxime was 52.7%.

Comparative Example 3

The reaction was conducted in the same manner as in Example 2, except that the silicic acid was not used. As a result, the conversion of the cyclohexanone was 68.0%, the selectivity to cyclohexanone oxime was 70.6% and the yield of cyclohexanone oxime was 48.0%.

Example 3

The continuous reaction was conducted in the same manner as in Example 1, except that the amount of the titanium silicate was changed from 0.9% by weight to 1% by weight based on the liquid portion of the reaction mixture. The increase of oxygen concentration in the gaseous portion due to the inactivation of the catalyst was not observed until the passage of reaction time was 16 hours. As a result of analysis of the liquid portion obtained after 15.5 hours of the reaction, the conversion of the cyclohexanone was 85.3%, the selectivity to cyclohexanone oxime was 96.7%, and the yield of cyclohexanone oxime was 82.5%.

Comparative Example 4

The continuous reaction was conducted in the same manner as in Example 1, except that the amount of the titanium silicate was changed from 0.9% by weight to 1% by weight based on the liquid portion of the reaction mixture, and the silica gel was not used. The increase of oxygen concentration in the gaseous portion due to the inactivation of the catalyst was observed when the passage of reaction time was 6 hours. As a result of analysis of the liquid portion obtained after 5.5 hours of the reaction, the conversion of the cyclohexanone was 87.6%, the selectivity to cyclohexanone oxime was 90.4%, and the yield of cyclohexanone oxime was 79.3%.

What is claimed is:

1. A method for producing a cyclohexanone oxime, the method comprising the step of reacting a cyclohexanone with hydrogen peroxide ammonia in the presence of a titanium silicate and at least one compound selected from the group consisting of a silica gel and a silicic acid.

2. The method according to claim 1, wherein the titanium silicate and the at least one compound are used in a concentration, respectively, of from about 0.1% by weight to about 10% by weight based on the liquid portion of the reaction mixture.

3. The method according to claim 1, wherein the reaction is conducted in the presence of water in an amount of about 10% by weight or more based the reaction mixture.

4. A method according to claim 1, wherein the at least one compound is silica gel.

5. The method according to claim 1, wherein the at least one compound is silicic acid.

\* \* \* \* \*